(12) United States Patent
Batchelor et al.

(10) Patent No.: US 9,782,216 B2
(45) Date of Patent: Oct. 10, 2017

(54) MEDICAL FORCEPS WITH VESSEL TRANSECTION CAPABILITY

(71) Applicant: GYRUS ACMI, INC., Southborough, MA (US)

(72) Inventors: Kester J. Batchelor, Mound, MN (US); Richard J. Curtis, Maple Grove, MN (US); Ryan J. Windgassen, Nowthen, MN (US)

(73) Assignee: GYRUS ACMI, INC., Southborough, MA (US)

( * ) Notice: Subject to any disclaimer, the term of this patent is extended or adjusted under 35 U.S.C. 154(b) by 0 days.

(21) Appl. No.: 15/044,201

(22) Filed: Feb. 16, 2016

(65) Prior Publication Data

US 2016/0278847 A1    Sep. 29, 2016

Related U.S. Application Data

(60) Provisional application No. 62/136,758, filed on Mar. 23, 2015.

(51) Int. Cl.
*A61B 18/14* (2006.01)
*A61B 17/285* (2006.01)
*A61B 18/00* (2006.01)

(52) U.S. Cl.
CPC ........ *A61B 18/1442* (2013.01); *A61B 17/285* (2013.01); *A61B 18/1445* (2013.01);
(Continued)

(58) Field of Classification Search
CPC ............ A61B 18/1442; A61B 18/1445; A61B 2018/00196; A61B 2018/1455;
(Continued)

(56) References Cited

U.S. PATENT DOCUMENTS 1,198,958  A   9/1916  Risely
2,042,985  A   6/1936  Gardella
(Continued)

FOREIGN PATENT DOCUMENTS

EP    0392548 A1   10/1990
EP    0724863 A2   8/1996
(Continued)

OTHER PUBLICATIONS

Search Report and Written opinion for International Application No. PCT/US2016/017995 dated Jun. 6, 2016.
(Continued)

*Primary Examiner* — Jaymi Della
*Assistant Examiner* — Eunhwa Kim
(74) *Attorney, Agent, or Firm* — The Dobrusin Law Firm, P.C.

(57) ABSTRACT

A surgical device includes a forceps and a blade. The forceps includes a first working jaw and a second working jaw. The blade extends along a longitudinal axis and includes a notched section. The blade is located between the first working jaw and the second working jaw. A first therapy current can be connected to the first working jaw, the second working jaw, or both so that tissue gripped between the first working jaw and the second working jaw and within the notched section can be coagulated. While the tissue is gripped between the first working jaw and the second working jaw, the blade is moveable along its longitudinal axis so that the tissue is cut with the notched section without repositioning the first working jaw, the second working jaw, or both.

18 Claims, 4 Drawing Sheets

(52) U.S. Cl.
CPC ............... *A61B 2018/00196* (2013.01); *A61B 2018/00428* (2013.01); *A61B 2018/00589* (2013.01); *A61B 2018/1412* (2013.01); *A61B 2018/1455* (2013.01)

(58) Field of Classification Search
CPC .. A61B 2018/00589; A61B 2018/1412; A61B 2018/00428
See application file for complete search history.

(56) References Cited

U.S. PATENT DOCUMENTS

| | | | |
|---|---|---|---|
| 2,214,984 A | 9/1940 | Bachmann |
| 2,381,084 A | 8/1945 | Slad |
| 2,575,652 A | 11/1951 | Bovee |
| 2,894,424 A | 7/1959 | Vaughan |
| 3,399,583 A | 9/1968 | Hall |
| 3,417,752 A | 12/1968 | Butler |
| 3,465,621 A | 9/1969 | Ladd |
| 3,576,072 A | 4/1971 | Foster |
| 3,643,663 A | 2/1972 | Sutter |
| 3,699,632 A | 10/1972 | Anhalt |
| 3,818,784 A | 6/1974 | McClure |
| 3,913,586 A | 10/1975 | Baumgarten |
| 4,041,952 A | 8/1977 | Morrison, Jr. et al. |
| 4,154,226 A | 5/1979 | Hennig et al. |
| 4,171,700 A | 10/1979 | Farin |
| 4,202,337 A | 5/1980 | Hren et al. |
| 4,318,313 A | 3/1982 | Tartaglia |
| 4,375,218 A | 3/1983 | DiGeronimo |
| 4,407,069 A | 10/1983 | Conners |
| 4,463,759 A | 8/1984 | Garito et al. |
| 4,492,231 A | 1/1985 | Auth |
| 4,492,832 A | 1/1985 | Taylor |
| 4,494,543 A | 1/1985 | Hart |
| 4,504,707 A | 3/1985 | Ochiai |
| 4,524,648 A | 6/1985 | Chung |
| 4,552,143 A | 11/1985 | Lottick |
| 4,669,470 A | 6/1987 | Brandfield |
| 4,686,980 A | 8/1987 | Williams et al. |
| 4,713,885 A | 12/1987 | Keklak et al. |
| 4,757,612 A | 7/1988 | Peyrot |
| 4,784,136 A | 11/1988 | Klein |
| 4,860,745 A | 8/1989 | Farin et al. |
| 4,896,661 A | 1/1990 | Bogert et al. |
| 4,935,027 A | 6/1990 | Yoon |
| 5,021,616 A | 6/1991 | Hardt |
| 5,035,695 A | 7/1991 | Weber, Jr. et al. |
| 5,071,426 A | 12/1991 | Dolgin et al. |
| 5,104,397 A | 4/1992 | Vasconcelos et al. |
| 5,108,392 A | 4/1992 | Spingler |
| 5,147,378 A | 9/1992 | Markham |
| 5,176,702 A | 1/1993 | Bales et al. |
| 5,190,541 A | 3/1993 | Abele et al. |
| 5,196,009 A | 3/1993 | Kirwan, Jr. |
| 5,207,691 A | 5/1993 | Nardella |
| 5,207,696 A | 5/1993 | Matwijcow |
| 5,208,983 A | 5/1993 | Masse |
| 5,226,904 A | 7/1993 | Gentelia et al. |
| 5,281,216 A | 1/1994 | Klicek |
| 5,290,286 A | 3/1994 | Parins |
| 5,342,359 A | 8/1994 | Rydell |
| 5,370,659 A | 12/1994 | Sakashita |
| 5,403,312 A | 4/1995 | Yates et al. |
| 5,423,814 A | 6/1995 | Zhu et al. |
| 5,425,743 A | 6/1995 | Nicholas |
| 5,440,813 A | 8/1995 | Roskam |
| 5,441,498 A | 8/1995 | Perkins |
| 5,445,638 A | 8/1995 | Rydell et al. |
| 5,456,695 A | 10/1995 | Herve Dallemagne |
| 5,458,598 A | 10/1995 | Fienberg et al. |
| 5,472,442 A | 12/1995 | Klicek |
| 5,483,952 A | 1/1996 | Aranyi |
| 5,499,998 A | 3/1996 | Meade |
| 5,531,744 A | 7/1996 | Nardella et al. |
| 5,540,685 A | 7/1996 | Parins et al. |
| 5,562,503 A | 10/1996 | Ellman et al. |
| 5,573,424 A | 11/1996 | Poppe |
| 5,626,577 A | 5/1997 | Harris |
| 5,665,100 A * | 9/1997 | Yoon ............... A61B 17/12013 606/139 |
| 5,702,390 A | 12/1997 | Austin et al. |
| 5,709,680 A | 1/1998 | Yates et al. |
| 5,735,849 A | 4/1998 | Baden et al. |
| 5,779,701 A | 7/1998 | McBrayer et al. |
| 5,797,941 A | 8/1998 | Schulze et al. |
| 5,810,805 A | 9/1998 | Sutcu et al. |
| 5,827,281 A | 10/1998 | Levin |
| 5,884,954 A | 3/1999 | Trozera |
| 5,891,140 A | 4/1999 | Ginn et al. |
| 5,902,301 A | 5/1999 | Olig |
| 5,922,001 A | 7/1999 | Yoon |
| 5,951,545 A | 9/1999 | Schilling et al. |
| 6,024,741 A | 2/2000 | Williamson, IV et al. |
| 6,030,384 A | 2/2000 | Nezhat |
| 6,039,734 A | 3/2000 | Goble |
| 6,050,996 A | 4/2000 | Schmaltz et al. |
| 6,053,908 A | 4/2000 | Crainich et al. |
| 6,074,386 A | 6/2000 | Goble et al. |
| 6,102,909 A | 8/2000 | Chen et al. |
| 6,110,171 A | 8/2000 | Rydell |
| 6,113,596 A | 9/2000 | Hooven et al. |
| 6,117,158 A | 9/2000 | Measamer et al. |
| 6,117,169 A | 9/2000 | Moe |
| 6,152,923 A | 11/2000 | Ryan |
| 6,190,386 B1 | 2/2001 | Rydell |
| 6,270,497 B1 | 8/2001 | Sekino et al. |
| 6,325,795 B1 | 12/2001 | Lidemann et al. |
| 6,358,268 B1 | 3/2002 | Hunt et al. |
| 6,402,747 B1 | 6/2002 | Lindemann et al. |
| 6,428,538 B1 | 8/2002 | Blewett et al. |
| 6,445,638 B1 | 9/2002 | Hsu et al. |
| 6,458,128 B1 | 10/2002 | Schulze |
| 6,464,704 B2 | 10/2002 | Schmaltz et al. |
| 6,486,419 B2 | 11/2002 | Horiguchi et al. |
| 6,494,886 B1 | 12/2002 | Wilk et al. |
| 6,514,252 B2 | 2/2003 | Nezhat et al. |
| 6,551,313 B1 | 4/2003 | Levin |
| 6,585,735 B1 | 7/2003 | Frazier et al. |
| 6,619,038 B2 | 9/2003 | Takada et al. |
| 6,623,499 B1 | 9/2003 | Andreini et al. |
| 6,641,595 B1 | 11/2003 | Moran et al. |
| 6,652,514 B2 | 11/2003 | Ellman et al. |
| 6,652,521 B2 | 11/2003 | Schulze |
| 6,679,882 B1 | 1/2004 | Kornerup |
| 6,689,130 B2 | 2/2004 | Arai et al. |
| 6,695,840 B2 | 2/2004 | Schulze |
| 6,726,686 B2 | 4/2004 | Buysse et al. |
| 6,749,610 B2 | 6/2004 | Kirwan, Jr. et al. |
| 6,752,767 B2 | 6/2004 | Turovskiy et al. |
| 6,808,525 B2 | 10/2004 | Latterell et al. |
| 6,827,717 B2 | 12/2004 | Brommersma et al. |
| 6,860,882 B2 | 3/2005 | Battles et al. |
| 6,926,716 B2 | 8/2005 | Baker et al. |
| 6,942,662 B2 | 9/2005 | Goble et al. |
| 7,083,613 B2 | 8/2006 | Treat |
| 7,094,231 B1 | 8/2006 | Ellman et al. |
| 7,108,694 B2 | 9/2006 | Miura et al. |
| 7,112,199 B2 | 9/2006 | Cosmescu |
| 7,147,637 B2 | 12/2006 | Goble |
| 7,150,749 B2 | 12/2006 | Dycus et al. |
| 7,156,846 B2 | 1/2007 | Dycus et al. |
| 7,232,440 B2 | 6/2007 | Dumbauld et al. |
| 7,244,257 B2 | 7/2007 | Podhajsky et al. |
| 7,252,667 B2 | 8/2007 | Moses et al. |
| 7,331,972 B1 * | 2/2008 | Cox ............... A61B 17/320016 606/170 |
| 7,344,536 B1 | 3/2008 | Lunsford et al. |
| 7,367,976 B2 | 5/2008 | Lawes et al. |
| 7,377,902 B2 | 5/2008 | Burbank |
| 7,481,810 B2 | 1/2009 | Dumbauld et al. |
| 7,503,917 B2 | 3/2009 | Sartor et al. |
| 7,604,635 B2 | 10/2009 | McClurken et al. |
| 7,625,391 B2 | 12/2009 | Kebel et al. |

(56) References Cited

U.S. PATENT DOCUMENTS

| | | |
|---|---|---|
| 7,674,261 B2 | 3/2010 | Garito et al. |
| 7,686,827 B2 | 3/2010 | Hushka |
| 7,722,607 B2 | 5/2010 | Dumbauld et al. |
| 7,744,615 B2 | 6/2010 | Couture |
| 7,753,909 B2 | 7/2010 | Chapman et al. |
| 7,758,577 B2 | 7/2010 | Nobis et al. |
| 7,789,878 B2 | 9/2010 | Dumbauld et al. |
| 7,879,035 B2 | 2/2011 | Garrison et al. |
| 7,896,875 B2 | 3/2011 | Heim et al. |
| 7,909,820 B2 | 3/2011 | Lipson et al. |
| 7,922,718 B2 | 4/2011 | Moses et al. |
| 7,931,668 B2 | 4/2011 | Sloat |
| 7,938,469 B2 | 5/2011 | Ait-Mani |
| 7,942,872 B2 | 5/2011 | Ein-Gal |
| 7,955,331 B2 | 6/2011 | Truckai et al. |
| 8,062,292 B1 | 11/2011 | Slater |
| 8,100,894 B2 | 1/2012 | Mucko et al. |
| 8,162,940 B2 | 4/2012 | Johnson et al. |
| 8,216,231 B2 | 7/2012 | Behl et al. |
| 8,226,649 B2 | 7/2012 | Falkenstein et al. |
| 8,246,094 B2 | 8/2012 | Long et al. |
| 8,251,989 B1 | 8/2012 | Newton et al. |
| 8,262,655 B2 | 9/2012 | Ghabrial et al. |
| 8,328,170 B2 | 12/2012 | Wasinger |
| 8,485,413 B2 | 7/2013 | Scheib et al. |
| 8,491,626 B2 | 7/2013 | Roy et al. |
| 8,496,603 B2 | 7/2013 | Mamourian |
| 8,512,371 B2 | 8/2013 | Kerr et al. |
| 8,568,410 B2 | 10/2013 | Vakharia et al. |
| 8,568,411 B2 | 10/2013 | Falkenstein et al. |
| 8,628,529 B2 | 1/2014 | Aldridge et al. |
| 8,882,756 B2 | 11/2014 | Greeley et al. |
| 2002/0099368 A1 | 7/2002 | Schulze |
| 2002/0106609 A1 | 8/2002 | Palermo et al. |
| 2003/0018331 A1 | 1/2003 | Dycus et al. |
| 2003/0050633 A1 | 3/2003 | Ellman |
| 2003/0097126 A1 | 5/2003 | Woloszko |
| 2003/0114850 A1 | 6/2003 | McClurken et al. |
| 2003/0144652 A1 | 7/2003 | Baker et al. |
| 2003/0181904 A1 | 9/2003 | Levine et al. |
| 2004/0030330 A1 | 2/2004 | Brassell et al. |
| 2004/0082946 A1 | 4/2004 | Malis |
| 2004/0097117 A1 | 5/2004 | Gonnering |
| 2005/0113824 A1 | 5/2005 | Sartor |
| 2005/0113825 A1 | 5/2005 | Cosmescu |
| 2005/0113827 A1 | 5/2005 | Dumbauld et al. |
| 2005/0187512 A1 | 8/2005 | Isola et al. |
| 2006/0084973 A1 | 4/2006 | Hushka |
| 2006/0190035 A1 | 8/2006 | Hushka et al. |
| 2006/0217701 A1 | 9/2006 | Young et al. |
| 2007/0043352 A1 | 2/2007 | Garrison et al. |
| 2007/0123855 A1 | 5/2007 | Morley et al. |
| 2007/0129716 A1 | 6/2007 | Daw et al. |
| 2008/0021450 A1* | 1/2008 | Couture .............. A61B 18/1442 606/51 |
| 2008/0033428 A1 | 2/2008 | Artale et al. |
| 2008/0147092 A1 | 6/2008 | Rogge et al. |
| 2008/0154300 A1 | 6/2008 | Jabbour |
| 2008/0236860 A1 | 10/2008 | Howe |
| 2008/0287948 A1 | 11/2008 | Newton et al. |
| 2009/0036887 A1* | 2/2009 | Hafner ................ A61B 18/1442 606/45 |
| 2009/0062786 A1 | 3/2009 | Garito et al. |
| 2009/0062792 A1 | 3/2009 | Vakharia et al. |
| 2009/0062830 A1 | 3/2009 | Hiraoka |
| 2009/0093804 A1 | 4/2009 | Newton |
| 2009/0138013 A1 | 5/2009 | Thorne et al. |
| 2009/0192509 A1 | 7/2009 | Curtis |
| 2010/0042096 A1 | 2/2010 | Ellman |
| 2010/0069940 A1 | 3/2010 | Miller et al. |
| 2010/0087814 A1 | 4/2010 | Desinger et al. |
| 2010/0137854 A1 | 6/2010 | Hosier |
| 2010/0228249 A1 | 9/2010 | Mohr |
| 2011/0045680 A1 | 2/2011 | Beller |
| 2011/0054462 A1 | 3/2011 | Ellman |
| 2011/0077648 A1 | 3/2011 | Lee et al. |
| 2011/0112530 A1 | 5/2011 | Keller |
| 2011/0178515 A1 | 7/2011 | Bloom et al. |
| 2011/0224669 A1 | 9/2011 | Podany |
| 2011/0319892 A1 | 12/2011 | Blomeyer |
| 2012/0022530 A1 | 1/2012 | Woodruff et al. |
| 2012/0078292 A1 | 3/2012 | Banju |
| 2012/0095460 A1 | 4/2012 | Rooks et al. |
| 2012/0101501 A1 | 4/2012 | Nishimura et al. |
| 2012/0123405 A1 | 5/2012 | Moua et al. |
| 2012/0150165 A1 | 6/2012 | Conley |
| 2012/0202388 A1 | 8/2012 | Selig |
| 2012/0253344 A1 | 10/2012 | Dumbauld et al. |
| 2013/0023874 A1 | 1/2013 | Lawes et al. |
| 2013/0066317 A1 | 3/2013 | Evans et al. |
| 2013/0079762 A1 | 3/2013 | Twomey et al. |
| 2013/0138096 A1 | 5/2013 | Benn |
| 2013/0178852 A1 | 7/2013 | Allen, IV et al. |
| 2013/0237982 A1 | 9/2013 | Rencher et al. |
| 2014/0236202 A1 | 8/2014 | Palmer et al. |
| 2014/0276772 A1 | 9/2014 | Batchelor et al. |
| 2014/0276785 A1 | 9/2014 | Batchelor et al. |
| 2014/0276786 A1 | 9/2014 | Batchelor |
| 2014/0276794 A1 | 9/2014 | Batchelor et al. |
| 2014/0276796 A1 | 9/2014 | Batchelor et al. |
| 2014/0276797 A1 | 9/2014 | Batchelor et al. |
| 2014/0276798 A1 | 9/2014 | Batchelor et al. |
| 2014/0276799 A1 | 9/2014 | Batchelor et al. |
| 2014/0276800 A1 | 9/2014 | Batchelor et al. |
| 2014/0276804 A1 | 9/2014 | Batchelor |
| 2015/0119885 A1 | 4/2015 | Windgassen et al. |
| 2015/0148798 A1 | 5/2015 | Windgassen et al. |

FOREIGN PATENT DOCUMENTS

| | | |
|---|---|---|
| EP | 1530952 A1 | 5/2005 |
| EP | 1810629 A2 | 7/2007 |
| EP | 1880685 A2 | 1/2008 |
| EP | 1977706 A1 | 10/2008 |
| WO | 2014/096815 A2 | 6/2014 |

OTHER PUBLICATIONS

Potentially related U.S. Appl. No. 14/829,725, filed Aug. 19, 2015.
Potentially related U.S. Appl. No. 14/830,069, filed Aug. 19, 2015.
Potentially related U.S. Appl. No. 14/830,255, filed Aug. 19, 2015.
Potentially related U.S. Appl. No. 14/177,780, filed Feb. 11, 2014.
Potentially related U.S. Appl. No. 14/178,411, filed Feb. 12, 2014.
Potentially related U.S. Appl. No. 14/209,071, filed Mar. 13, 2014.
Potentially related U.S. Appl. No. 14/205,919, filed Mar. 12, 2014.
Potentially related to U.S. Appl. No. 14/206,010, filed Mar. 12, 2014.
Potentially related U.S. Appl. No. 14/210,535, filed Mar. 14, 2014.
Potentially related U.S. Appl. No. 14/210,741, filed Mar. 14, 2014.
Potentially related U.S. Appl. No. 14/211,042, filed Mar. 14, 2014.
Potentially related U.S. Appl. No. 14/178,569, filed Feb. 12, 2014.
Potentially related U.S. Appl. No. 14/178,577, filed Feb. 12, 2014.
315MHZ sliding remote cover, available at website: http://www.aliexpress.com/item/Sliding-Cover-Gate-Remote-Control-Duplicator-Adjustable-Frequencey-Remote-Copy-100pCS-lot-Free-Shipping-by-DHL/566451354.html?tracelog=back_to_detail_a (accessed on Feb. 21, 2013).
Sliding Gate Remote Control Duplicator, available at website: http://www.aliexpress.com/item/315MHZ-sliding-cover-remote-controller-duplicating-remote-controller-sliding-gate-remote-garager-door-remote/4917955542.html (accessed on Feb. 21, 2013).
International Search and Written Opinion for Application No. PCT/US2014/023958 dated Jul. 21, 2014.
International Search Report and Written Opinion for Application No. PCT/US2014/024134 dated Apr. 30, 2014.

(56) References Cited

OTHER PUBLICATIONS

International Search Report and Written Opinion for Application No. PCT/US2014/024197 dated Jul. 21, 2014.
International Preliminary Report on Patentability Application No. PCT/US2014/023958, dated Mar. 5, 2015.

* cited by examiner

MEDICAL FORCEPS WITH VESSEL TRANSECTION CAPABILITY

FIELD

The present teachings relate to medical forceps, and more particularly to medical forceps for clamping, coagulating, and transecting a vessel or tissue.

BACKGROUND

Generally, medical forceps are plier-like devices that include opposing jaws for clamping, manipulating, and/or pulling a vessel or tissue during a surgical procedure. One or both of the opposing jaws can also be provided with electrosurgical energy (i.e., a therapy current) so that the vessel or tissue can be cauterized or coagulated while clamped between the jaws. More specifically, monopolar forceps utilize one active electrode and a remote patient return pad that is attached externally to the patient. When the electrosurgical energy is applied, the energy travels from the active electrode to the vessel or tissue to cauterized or coagulate the vessel or tissue, through the patient, and to the return pad. Bipolar forceps utilize two opposing electrodes, each of which are charged to a different electric potential. Because a vessel or tissue is a conductor of electrical energy, when the opposing jaws grasp the vessel or tissue, the electrical energy is transferred through the vessel or tissue to cauterized or coagulate the vessel or tissue.

Some surgical procedures also require the vessel or tissue to be cut, transected, cauterized, or coagulated with a blade. For this, generally, an ancillary medical device or blade may be required. However, an ancillary blade may undesirably require additional space at the surgical site to store the ancillary device. Moreover, using an ancillary blade may undesirably require additional hand movements by the surgeon performing the procedure (i.e., to pick up the device, use the device, and put the device back down), and may undesirably add additional time to the medical procedure.

Some examples of medical forceps can be found in U.S. Pat. Nos. 5,445,638, 7,232,440, and 8,568,410, all of which are incorporated by reference herein in their entirety for all purposes. It would be desirable to have a combination medical device for cauterizing or coagulating a vessel or tissue and then subsequently cutting the vessel or tissue. It would be desirable to have a medical device capable of clamping a vessel or tissue, subsequently cauterizing or coagulating the vessel or tissue, and then cutting the vessel or tissue with a single device without repositioning or reconfiguring the device. It would be desirable to have a medical device capable of clamping a vessel or tissue, subsequently cauterizing or coagulating vessel or tissue, and then cutting the vessel or tissue with a blade member by moving the blade relative to the medical device in a proximal direction, a distal direction, or both. It would be desirable to have a medical device including a pair of clamping jaws and a blade that can be rotated between to the jaws. It would be desirable to have a medical device where surgeons can more readily and more easily produce consistent, high quality transections while limiting movement of the blade and/or the jaws. It would be attractive to have a medical device including forceps and an electrode that extends beyond a distal end of the gripping assembly in a neutral or steady state. It would be attractive to have a medical device including forceps and an electrode that further extends beyond a distal end of the gripping assembly or retracts to cut a vessel or tissue. What is needed is a medical device including forceps and a blade that is also an electrode or includes a separate electrode member.

SUMMARY

The present teachings meet one or more of these needs by providing a device, a surgical device, or an electrosurgical device comprising forceps and a blade. The forceps includes a first working jaw and a second working jaw. The blade extends along a longitudinal axis and includes a notched section. The blade is located between the first working jaw and the second working jaw. A first therapy current is connected to the first working jaw, the second working jaw, or both so that tissue gripped between the first working jaw and the second working jaw and within the notched section can be coagulated. While the tissue is gripped between the first working jaw and the second working jaw, the blade is moveable along its longitudinal axis so that the tissue is cut with the notched section without repositioning the first working jaw, the second working jaw, or both.

The present teachings also provide an electrosurgical device comprising forceps including a first working jaw, a second working jaw, and a blade electrode located between the first working jaw and the second working jaw. The blade electrode includes a notched section having a proximal edge, a distal edge and a receiving region therebetween. The first working arm, the second working arm, or both are connected to a first therapy current so that during an application of the first therapy current, tissue located within the receiving region and gripped between the first working jaw and the second working jaw is coagulated. The blade electrode is moveable so that the tissue located within the receiving region of the notched section is cut with either the proximal edge or the distal edge without repositioning the forceps. The blade electrode is connected to a second therapy current so that during an application of the second therapy current, the blade electrode functions as an electrosurgical blade when at least a portion of the blade electrode extends beyond a distal end of the forceps.

The present teachings further provide a method, comprising providing an electrosurgical device including forceps having a first working jaw and a second working jaw. The method includes a step of providing a blade member between the first working jaw and the second working jaw, the blade member extending along a longitudinal axis and including a notched section having a proximal edge and a distal edge with a receiving region therebetween. The method includes a step of providing a first therapy current to the first working jaw, the second working jaw, or both; and placing tissue between the first working jaw and the second working jaw. The method includes a step of positioning the tissue within the receiving region; gripping the tissue between the first working jaw and the second working jaw and coagulating the tissue therebetween; and moving the blade member while the tissue is gripped without repositioning the forceps so that the tissue is transected with the notched section.

Further yet, the present teachings provide a medical device that solved all of the aforementioned problems and deficiencies. The present teachings provide a combination medical device for cauterizing or coagulating a vessel or tissue and then subsequently cutting the vessel or tissue. The present teachings provide a medical device capable of clamping a vessel or tissue, subsequently cauterizing or coagulating the vessel or tissue, and then cutting the vessel or tissue with a single device without repositioning or reconfiguring the device. The present teachings provide a medical device capable of clamping a vessel or tissue, subsequently cauterizing or coagulating vessel or tissue, and then cutting the vessel or tissue with a blade member by moving the blade relative to the medical device in a proximal direction, a distal direction, or both. The present teachings provide a medical device including a pair of clamping jaws and a blade that can be rotated between to the jaws. The present teachings provide a medical device where surgeons can more readily and more easily produce consistent, high quality transections while limiting movement of the blade and/or the jaws. The present teachings provide a medical device including forceps and an electrode that extends beyond a distal end of the gripping assembly in a neutral or steady state. The present teachings provide an electrode that further extends beyond a distal end of the gripping assembly or retracts to cut a vessel or tissue. The present teachings provide a medical device including forceps and a blade that is also an electrode or includes a separate electrode member.

DETAILED DESCRIPTION

This Application claims priority to U.S. Provisional Application No. 62/136,758 filed on Mar. 23, 2015, the entirety of which is hereby incorporated by reference herein for all purposes. The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to and provide a forceps device. The forceps may function to grip an object. Preferably, the forceps may be a medical device or instrument used during surgery to grip an item or feature of interest, such as a part of a body, an anatomical feature, tissue, veins, arteries, or a combination thereof. The forceps may be used in surgery, for example in laparoscopic surgery. The forceps may be used with or without power. That is, current or electrosurgical energy can be passed through the forceps so that the forceps can be used for electrosurgery. For example, a therapy current may be passed from a first jaw member to a second jaw member (or vice versa) while a vessel or tissue is located between the jaw members so that the therapy current can coagulate blood, cauterize tissue, transect tissue, or a combination thereof (i.e., bipolar configuration). Alternatively, or in addition to, a therapy current can be passed from one of the jaw members to a remote electrode (e.g., a return pad) while a vessel tissue is located between the jaw members so that the therapy current can coagulate blood, cauterize tissue, transect tissue, or a combination thereof (i.e., monopolar configuration).

The forceps may generally include one or more working assemblies and sufficient controls and/or mechanisms for using, controlling, and/or actuating the one or more working assemblies. The forceps may generally include a gripping assembly for gripping, holding, manipulating, pulling, coagulating, cauterizing, cutting, or a combination thereof a feature of interest. The forceps may generally include a cutting assembly for gripping, holding, manipulating, coagulating, cauterizing, cutting, or a combination thereof a feature of interest. The forceps may include all of the parts needed to adequately, effectively, and efficiently perform the recited functions of the working assemblies. The forceps may include the parts needed to move the gripping assembly between an open position and a closed or clamped position. The forceps may include the parts needed to move the blade cutting assembly so that tissue gripped or clamped between the jaw members can be cut, transected, cauterized, coagulated, and/or sealed. The forceps may include the parts necessary for the gripping assembly, the blade, the separate blade electrode, or a combination thereof to function as one or more electrosurgical devices. Generally, the forceps may include a stylet (e.g., a tubular member, a hollow tube, or an assembly of tubes), a hand piece, one or more operable mechanisms used to actuate the stylet, and a means (i.e., a cord) for connecting the forceps to a source of electrosurgical energy (i.e., a generator, a battery powered device, or both) so that the forceps can function as electrosurgical forceps. Further details of the forceps and the working assemblies and mechanisms of the forceps can be found herein and in U.S. Patent Publication Number 2014/0276795 A1 filed Mar. 12, 2014; U.S. patent application Ser. No. 14/484,341 filed on Sep. 12, 2014; and U.S. patent application Ser. No. 14/484,404 also filed on Sep. 12, 2014, all three of which are incorporated in their entirety herein.

The hand piece may function to form, create, or provide an enclosing structure for the forceps of the present teachings. The hand piece may function to form, create, or provide a gripping portion for the user to handle, manipulate, and/or use the forceps. The hand piece may be any device that houses the working assemblies, components, and/or parts required for the forceps and the working assemblies to function. The hand piece may assist in performing laparoscopic surgery. The hand piece may be ergonomically shaped. The ergonomic shape of the hand piece may be any shape so that the forceps may be used ambidextrously. The ergonomic shape of the hand piece may be any shape such that all of the controls and mechanisms for using the forceps can be accessed by a single hand gripping the hand piece.

The gripping assembly may function to create and/or maintain a gripping force; grip a feature of interest; or both. The gripping assembly may be any part or combination of parts that may be actuated and used during a medical procedure to grip one or more features of interest, like a vessel, tissue, vein, artery, or a combination thereof. The gripping assembly may function to create a sufficient gripping force so that one or more features of interest can be gripped, manipulated, pulled, secured, cauterized, coagulated, or a combination thereof without tearing, ripping, and/or otherwise damaging the one or more features of interest. The gripping assembly may function to create a sufficient gripping force so that one or more features of interest can be gripped without damaging the one or more features of interest so that the jaws do not touch one another and cause an electrical fault and/or a short circuit. The gripping assembly may be actuated between a closed, clamping, or gripping position, and an open position via one or more levers, triggers, knobs, buttons, wheels, the like, or a combination thereof located on the hand piece, the forceps, or both. The gripping assembly may be actuated via one or more controls and/or mechanisms. The gripping assembly may be actuated so that one or more parts move, close, pivot, clamp, or a combination into a closed, clamping, or gripping position to create a gripping force. The gripping assembly may be actuated by retracting or moving the two or more opposing jaws (i.e., the upper jaw and the lower jaw) proximally into the one or more tubular members so that the two opposing jaws are biased towards one another and close into the gripping position to create a gripping force. In the closed or gripping position, the gripping portion of the opposing jaw members may be in contact, or may be in a slight spaced relation relative to one another. The gripping assembly may be actuated by extending or moving the two opposing jaws (i.e., the upper jaw and the lower jaw) distally out of or away from the one or tubular members so that the two opposing jaws move or pivot away from one another into the open position to release the gripping force. In the open position, the jaw members may be in spaced relation to one another so that an item or feature of interest can be placed between the jaw members or removed from between the jaw members. The gripping assembly may be rotated or rotatable when the gripping assembly is in the open position, the closed position, or both. The gripping assembly may be rotatable about an axis (e.g., a rotational axis of the gripping assembly, a longitudinal axis of the gripping assembly, a longitudinal axis of the tubular member, a longitudinal axis of the blade or separate electrode member, or a combination thereof). The gripping assembly may be moved (i.e., laterally, axially, radially, proximally, distally, longitudinally, or a combination thereof) when the gripping assembly is in the open position, in a closed position, or both. An electrosurgical current or therapy current can be selectively passed from a first jaw member to a second jaw member (or vice versa) when tissue is located therebetween so that the therapy current can coagulate blood, cauterize tissue, transect tissue, or a combination thereof. A therapy current can be passed from one or more of the jaw members to a remote electrode (e.g., a return pad) while tissue is located between the jaw members so that the therapy current can coagulate blood, cauterize tissue, transect tissue, or a combination thereof. The gripping assembly may be generally comprised of two or more opposing jaw members.

The two or more opposing jaw members may function to create a gripping force. The two or more opposing jaw members may move or pivot towards each other to create a gripping force to grip a feature of interest; to cut, coagulate, cauterize, or transect a feature of interest; or a combination thereof. The two or more opposing jaw members may move away from each other to release a gripping force; release a previously gripped feature of interest; or both. The two or more opposing jaws may be any device(s) that may be used to grip or clamp an item of interest for coagulating, cauterizing, sealing, cutting, transecting, or a combination thereof. The two or more opposing jaws may be any structure(s) or member(s) that may allow for one jaw to be static and one jaw to be movable; for both jaws to be moveable; or any combination thereof. One or both of the jaws may include a pivot axis so that one or both of the opposing jaws can move or pivot about the pivot axis to perform a gripping function and grip or hold an item of interest without damaging the item of interest. That is, one jaw member may pivot towards another jaw member that is static or non-pivoting to perform a gripping function. Alternatively, both jaws may pivot towards one another to perform a gripping function. One or both of the jaws may include a pivot axis so that one or both of the opposing jaws can more or pivot about the pivot axis to perform a releasing function to release a gripped item or feature of interest. That is, one jaw member may pivot away from another jaw member that is static or non-pivoting. Alternatively, both jaws may pivot way from one another. The two opposing jaws may be biased from an open position to a closed position by retracting one of the one or more jaw members into the tubular member; moving one or more tubular members towards a distal end of the jaw members; or both. The jaw members may include a ramped surface, a raised surface, one or more arcuate sections, or a combination thereof that are sufficiently large so that the arcuate sections do not fit within the tubular member. Preferably, at least a portion of the laterally extending arcuate sections are wider than an opening of the tubular member so that axial movement of the tubular member, the jaws, or both bias the two opposing jaws to close the two opposing jaws, create a gripping force, or both. The one or more jaws may be free of one or more arcuate segments. The two or more opposing jaws may be made of a material that is at least partially flexible, resilient, rigid, stainless, plastically deformable, or a combination thereof. The two or more opposing jaws may be made of a material that conducts electricity. The two or more opposing jaws may apply electricity, current, a therapy current, or a combination thereof to a feature of interest that is gripped, placed, held, and/or located between the two or more opposing jaws. That is, a therapy current can be selectively passed from a first jaw member to a second jaw member (or vice versa) when tissue is located therebetween so that the therapy current can coagulate blood, cauterize tissue, transect tissue, or a combination thereof. A therapy current can be passed from one or more of the jaw members to a remote electrode (e.g., a return pad) while tissue is located between the jaw members so that the therapy current can coagulate blood, cauterize tissue, transect tissue, or a combination thereof. The two or more opposing jaws may be electrically isolated from one another so that bipolar electrosurgical energy can be effectively transferred through the tissue or vessel gripped between the jaw members to seal or coagulate the tissue or vessel. The two or more opposing jaws may be automatically switched to function as electrosurgical forceps once the jaws are in a closed position. A user may manually select the two or more opposing jaws to function as electrosurgical forceps before the jaws are in a closed or clamped position (i.e., when the jaws are in an open position), or after the jaws are in the closed position.

The two or more opposing jaw members may include a gripping surface or gripping portion for gripping an item of interest. The gripping portion of the two or more opposing jaws may have a surface texture to grip a feature of interest. For instance, the surface texture may be at least partially smooth, flat, contoured, serrated, textured, horizontal, vertical, planar, canted, rolling, irregular, or a combination thereof. The one or more jaws may include one or more ridges, mouse teeth, gaps, openings, of a combination thereof. The two or more opposing jaws may each be generally U-shaped, C-shaped, S-shaped, may be linearly shaped, irregularly shaped, rounded, the like, or a combination thereof. One or both of the jaw members may include one or more openings.

The one or more openings in the one or more jaw members may function so that one or more operable mechanisms, blades, separate blade electrodes, or a combination thereof can extend beyond the gripping assembly, or be extended beyond the gripping assembly. The one or more openings may function so that or more operable mechanisms, blades, separate blade electrodes, or a combination thereof can be moved to extend past a distal end of the gripping assembly while the gripping assembly is in an open position, a closed or clamped position, or both. The one or more openings may function so that or more operable mechanisms, blades, separate blade electrodes, or a combination thereof can remain extended beyond a distal end of the gripping assembly in a steady state position regardless if the gripping assembly is in an open position, a closed position, or both. The one or more openings may provide for the one or more blades, separate blade electrodes, or both to be retracted into the gripping assembly when the gripping assembly is in an open or closed position so that the blade, separate blade electrode, or both do not protrude or extend beyond a distal end of the griping assembly. The one or more openings may be dimensioned so that or more operable mechanisms, blades, separate blade electrodes, or a combination thereof can be moved there through, rotated therein, or a combination thereof without moving or repositioning the gripping assembly. The one or more openings may be a gap, a notch, a cutout, a recess, an aperture, an orifice, or a combination thereof. The one or more openings may be located at a distal end of the gripping assembly. The one or more openings may be located in an upper surface, a lower surface, or on any surface of the gripping assembly so that the aforementioned functions can be performed. One or both of the jaw members may include one or more blade tracks.

The one or more blade tracks may be any shape and size so that a blade, a functional element, a surgical instrument, a separate blade electrode, or a combination thereof can move or extend between the jaw members. The one or more blade tracks may provide for a blade, a separate blade electrode, or both to move to cut, transect, cauterize, and/or coagulate a vessel or tissue grasped between the opposing jaw members. The one or more blades, separate blade electrodes, or both may be located and move within the same blade track; may be located and move in separate blade tracks; or a combination thereof. The one or more bade tracks may provide for a blade, a separate blade electrode, or both to be positioned, actuated, extended, retracted, reciprocated, moved, rotated, or a combination thereof relative to the gripping assembly while the gripping assembly is in a closed position, an open position, or both. The one or more blade tracks may provide for one or more of the blades, blade electrodes, or both to extend beyond a distal end of the gripping assembly in a steady state condition, regardless if the gripping assembly is in an open position or a closed position. The one or more blade tracks may be generally parallel to one another, may extend in a non-parallel relationship, or a combination of both. A portion of the one or more blade tracks may be located in or extend in the first or upper jaw member. A second complementary portion of the one or more blade tracks may be located in or extend in the opposing jaw member. The one or more blade tracks may be located entirely in one or both of the jaw members. The one or more blade tracks may be configured as one or more straight slots with no degree of curvature, or, may be dimensioned to include some curvature. The one or more blade tracks may be irregularly shaped, curved, straight, linear, angled, drafted, or a combination thereof. The one or more blade tracks may complement the general shape of the one or more blades, separate electrode members, or both. The one or more blade tracks may be one or more notches, grooves, channels, troughs, recesses, the like, or a combination thereof. The one or more blade tracks may be electrically isolated from the one or more blades, separate blade electrodes, jaw members, or a combination thereof.

The one or more blades may function to cut, transect, cauterize, coagulate, or a combination thereof a feature or area of interest. The one or more blades may be any cutting tool, blade, electrode, blade electrode, scalpel, knife, and/or separate member that may be used in or used during a medical or surgical procedure. The one or more blades may be any cutting device that may be extended and retracted through the one or more tubular members, the gripping assembly, one or more openings in the gripping assembly, the blade track, or a combination thereof. The one or more blades may be in sliding communication with the one or more blade tracks. The one or more blades may be selectively reciprocated to cut a feature of interest located, gripped, or placed between the jaw members. The one or more blades may be made of any material that may be sharpened; is strong enough to cut tissue, veins, arteries, an anatomical feature, a feature of interest, or a combination thereof; is biocompatible; may conduct electricity; or a combination thereof. The one or more blades, the distal end of the one or more blades, or both, may conduct energy so that the one or more blades, the distal end, or both can be used as a blade electrode. The distal end of the one or more blades may be sharp for cutting an object, item, or feature of interest with or without power. The distal end of the one or more blades may be dull or not sharp, which may be preferred in some applications to prevent unintentional cutting and/or transecting of an item or feature during handling and/or manipulation of the medical instrument. This may be especially preferred in electrosurgical configurations where the cutting or transecting of the item or feature of interest is performed with a therapy current. The distal end of the one or more blades may be curved, linear, angled, or irregularly shaped. For example, the distal end of the blade may be canted or slanted proximally or distally. The one or more blades may be any shape that may generally fit inside the inner or hollow portion of the tubular member and may extend into the gap formed between the two opposing jaw members, a gap formed at the distal end of the gripping assembly, the opposing jaw members, or a combination thereof. The one or more blades may be sufficiently small so that they may be housed within the tubular member. The one or more blades may rotate, or may be rotatable about a blade axis, a longitudinal axis, a jaw axis, a tubular axis, a forceps axis, a separate blade electrode axis, or a combination thereof. The one or more blades may be rotated while the gripping assembly is in a closed position, an open position, or a position therebetween. The one or more blades may be rotated while the blade is being advanced and/or retracted. Preferably, the one or more blades may be static (i.e., non-rotatable) while in motion. The one or more blades may be static or non-rotatable and the notched or receiving region may face the first or upper jaw member. The one or more blades may be static or non-rotatable and the notched or receiving region may face the second or lower jaw member. The one or more blades may be static or non-rotatable and the notched or receiving region may face a region or direction between the first or upper jaw member and the second or lower jaw. The one or more blades may be rotated so that a notched or receiving region faces a first or upper jaw member, faces a second or lower jaw member, or faces a position between the first and second jaw member. The one or more blades may be rotated so that an upper edge of the notched or receiving region faces one of the jaw members, or faces a direction between the jaw members. The one or more blades may be extended into and/or retracted from the opening, gap, or track formed between the two opposing jaw members. The one or more blades, the distal end of the one or more blades, or both may extend beyond a distal end of the forceps, the gripping assembly, the jaw members, or a combination thereof when the one or more blades are in a steady state, or in a non-cutting position. The one or more blades, the distal end of the one or more blades or both may permanently extend beyond a distal end of the gripping assembly. The one or more separate blade electrodes may permanently extend beyond a distal end of the forceps, the gripping assembly, the jaw members, or a combination thereof and restricted from moving relative to the gripping assembly, jaw members, one or more other blades, or a combination thereof. The one or more blades, distal end(s) of the one or more blades, or both may be moved so that a distal end of the one or more blades extends distally from the medical forceps, the gripping assembly, or both when the cutting assembly is in a cutting position, a non-cutting position, or in a position therebetween. The one or more blades may be coupled directly to a mechanism such as a cutting trigger, a rotation wheel, a gripping trigger or a combination thereof. The one or more blades may be coupled to one or more of the aforementioned mechanisms via one or more support rods, camming sections, or both so that a user can move the one or more cutting blades. The one or more blades may be elongated members that extend along a blade longitudinal axis, a blade track axis, a tubular member axis, or a combination thereof. The one or more blades may be any length. The one or more cutting blades may include one or more notched sections.

The one or more notched sections may function to cut a feature of interest (e.g., tissue, veins, arteries, an anatomical feature, or a combination thereof). The one or more notched sections may function to cut a feature of interest while the gripping assembly is in a closed position, an open position or both. The one or more notched sections may function to cut or transect tissue or a vessel after coagulating or sealing the tissue or vessel without having to reposition the forceps, the gripping assembly, the jaw members, or a combination thereof. In other words, the tissue or vessel can be cut or transected without having to open, re-grip, or re-configure the vessel or tissue after gripping with the gripping assembly or between the jaw members. The one or more notched sections may function to receive one or more features of interest. The one or more notched sections may be or may include one or more recessed sections, slotted sections, open sections, angled sections, or a combination thereof. The one or more notched sections may be generally rectangular-shaped, square-shaped, oval-shaped, irregularly shaped, or a combination thereof. The one or more notched sections may include one or more edges. The one or more notched sections may include one or more proximal edges, distal edges, upper edges, or a combination thereof. It is understood that the upper edge may be a lower edge depending on the orientation of the blade and the frame of reference selected. Likewise, the proximal edge may be the distal edge depending on the orientation of the blade and the frame of reference selected. The one or more edges may be sharp so that an item or feature of interest can be cut or transected with the one or more sharp edges. The item or feature of interest can be cut with the one or more sharp edges with or without applying power or a therapy current. One or more of the edges may be blunt. That is, one or more of the edges may be dull or not sharp, which may be preferred in some applications to prevent unintentional cutting and/for transecting of an item or feature during handling and/or manipulation of the medical instrument. This may be especially preferred in electrosurgical configurations where the cutting or transecting of the item or feature of interest is performed with a therapy current. The one or more proximal edges, distal edges, and/or upper edges can be used to cut a feature of interest when the blade is moved, rotated, extended, retracted, or a combination thereof. The one or more distal edges and/or upper edges may cut a feature of interest when the blade is moved proximally relative to a distal end of the gripping assembly. The one or more proximal edges and/or upper edges may cut a feature of interest when the blade is moved distally relative to a distal end of the gripping assembly. The one or more proximal edges distal edges, and/or upper edges may be generally straight, curved, arcuate, irregular, or a combination thereof. The proximal edge, the distal edge, or both, may extend generally perpendicular relative to a longitudinal axis of the blade and/or relative to a longitudinal axis along which the blade moves. The proximal edge, the distal edge or both may be generally canted or slanted relative to the longitudinal axis. One of the proximal edge and the distal edge may be generally canted or slanted relative to the longitudinal axis, while the other of the proximal edge and the distal edge may be generally perpendicular relative to the longitudinal axis. The proximal edge and/or the distal edge may be canted proximally or canted distally relative to a distal end of the blade or relative to the handle of the device. The upper edge may extend generally parallel to the longitudinal axis, or the upper edge may extend at a cant or slant proximally or distally relative to the longitudinal axis and the distal end of the blade or the handle of the device. The one or more notched sections may define a receiving region for receiving tissue or a vessel. The one or more notched sections rosy allow for a vessel or tissue to be gripped with the gripping surfaces without interfering with the blade. That is, the recessed section may clear the one or more jaw members when the gripping assembly is in the gripping position. In other words, the upper edge of the notched section may be located within one of the jaws so that the upper edge does not contact the vessel or tissue when gripped and the gripping assembly is in a closed or clamped position. The upper edge of the notched section may contact the vessel or tissue when gripped and the gripping assembly is in a closed position. The blade may be rotated independently of the gripping assembly so that the one or more proximal edges distal edges, and/or upper edges faces the upper jaw member, the lower jaw member, or face a position therebetween so that a surgeon can cut or transect tissue with the notched section facing upwardly, downwardly, or in a position therebetween. The one or more notched sections may define one or more receiving regions. The one or more receiving regions may function to receive one or more feature or items of interest. The one or more receiving regions may be dimensioned so that an item or feature of interest can be placed or received therein without contacting the one or more proximal edges distal edges, and/or upper edges when the gripping assembly is in a closed or clamped position, an open or receiving position, or both. The one or more blades may include one or more separate blade electrodes.

The one or more separate blade electrodes may function to coagulate, cauterize, cut, transect, or a combination thereof an item or feature of interest. The one or more separate blade electrodes may be in sliding communication with the one or more blade tracks. The one or more separate blade electrodes may be selectively reciprocated to extend beyond a distal end of the gripping assembly to cut, coagulate, cauterize, or a combination thereof a feature of interest. The one or more separate blade electrodes may be made of any material that may be sharpened; is biocompatible; may conduct electricity; or a combination thereof. The one or more separate blade electrodes may be any shape that may generally fit inside the inner or hollow portion of the tubular member and may extend into the gap formed between the two opposing jaw members, a gap formed at the distal end of the gripping assembly, the opposing jaw members, or a combination thereof. The one or more separate blade electrodes may rotate, or may be rotatable about a blade axis, a longitudinal axis, a jaw axis, a tubular axis, a forceps axis, a separate blade electrode axis, or a combination thereof. The one or more separate blade electrodes may be moved or rotated while the gripping assembly is in a closed or clamping position, an open position, or both. The one or more separate blade electrodes may be extended into and/or retracted from the opening, gap, or track formed between the two opposing jaw members. The one or more separate blade electrodes may extend beyond a distal end of the forceps, the gripping assembly, the jaw members, or a combination thereof in a steady state position. The one or more separate blade electrodes may extend beyond a distal end of the forceps, the gripping assembly, the jaw members, or a combination thereof in a steady state position and may be retracted or moved proximally into the gripping assembly. The one or more separate blade electrodes may permanently extend beyond a distal end of the forceps, the gripping assembly, the jaw members, or a combination thereof. The one or more separate blade electrodes may be moved so that a distal end of the one or more separate blade electrodes extends distally from the medical forceps, the gripping assembly, or both. The one or more separate blade electrodes may be coupled directly to a cutting trigger, a rotation wheel, a gripping trigger or a combination thereof, or may be coupled thereto via one or more support rods, camming sections, or both so that a user can move the one or more separate blade electrodes. The one or more separate blade electrodes may extend along a longitudinal axis. The one or more separate blade electrodes may be any length. The one or more separate blade electrodes may include a distal end that is sharp; may include one or more notched sections including a proximal edge, a distal edge, and an upper edge, one or more of which may be sharp; or a combination thereof. The one or more separate blade electrodes may be configured to cut and/or transect a vessel or tissue. One or more therapeutic currents may be supplied to the one or more separate blade electrodes so that the separate blade electrode(s) can function as an electrosurgical blade, a blade electrode, or both. One or more therapeutic currents may be supplied to the one or more separate blade electrodes so that a distal end of the separate blade electrode(s) can function as a blade electrode when the blade extends beyond a distal end of the gripping assembly. The one or more separate blade electrodes may be automatically switched to function as a blade electrode once a distal end of the separate blade electrode is extended beyond a distal end of the gripping assembly. A user may select the one or more separate blade electrodes to function as an electrode member once a distal end of the blade extends beyond a distal end of the gripping assembly. The one or more separate blade electrodes can be activated as a monopolar electrode before the separate blade electrodes is advanced past a distal end of the gripping assembly, while the blade is advanced, or after the blade is advanced. The one or more separate blade electrodes may be electrically isolated from the jaw members, the blade, the cutting assembly, or a combination thereof so that as the one or more separate blade electrodes move, or the one jaw member(s) move, the one or more separate blade electrodes, jaw members, and blades are not in contact.

One or more therapeutic currents may be supplied to the one or more blades, the one or more separate blade electrodes, or both so that the blade(s), the separate blade electrode(s) can function as an electrosurgical blade, a blade electrode, or both. One or more therapeutic currents may be supplied to the one or more blades, the one or more separate blade electrodes, or both so that a distal end of the blade, separate blade electrode, or both can function as a blade electrode when extended beyond a distal end of the gripping assembly. In this regard, the blade, the separate blade electrode, or both may function as a combination cutting device and electrode member. The one or more blades, the one or more separate blade electrodes, or both, may be automatically switched to function as a blade electrode once a distal end of the blade is extended beyond a distal end of the gripping assembly. A user may select the one or more blades, the one or more separate blade electrodes, or both to function as an electrode member once a distal end of the blade extends beyond a distal end of the gripping assembly. The one or more blades, the one or more separate blade electrodes, or both can be activated as a monopolar electrode or blade before the blade is advanced past a distal end of the gripping assembly, while the blade is advanced, or after the blade is advanced. One or more therapeutic currents may be supplied to the one or more blades, the one or more separate blade electrodes, or both so that the blade can function as a monopolar blade, a bipolar blade, or both. The one or more blades, the one or more separate blade electrodes, or both may be electrically isolated from the jaw members so that when the one or more blades move, or the one jaw member(s) move, the one or more blades and the jaw members are restricted or prevented from contacting.

Figure 1:
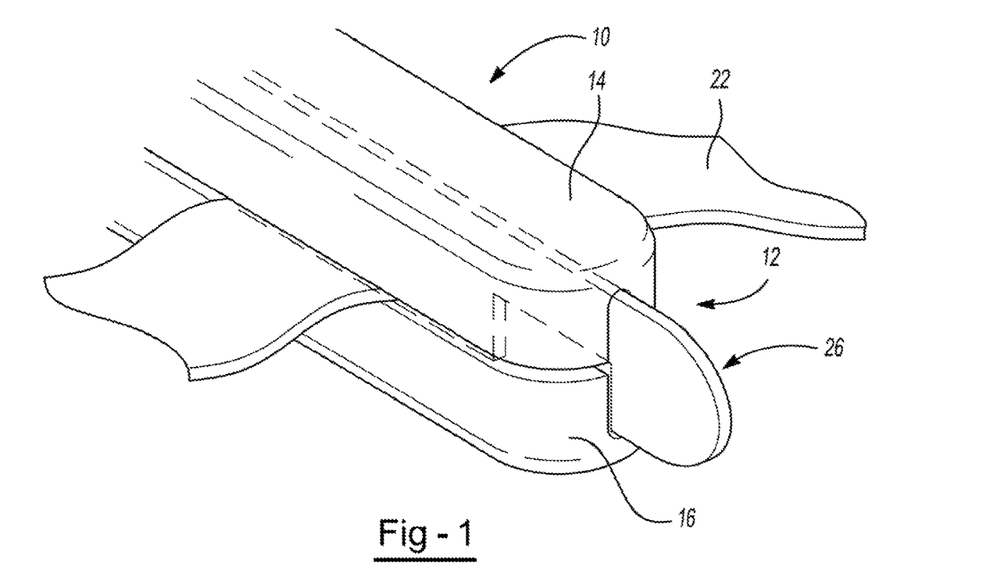
FIG. 1 is a partial perspective view of the forceps according to the teachings herein.

FIG. 1 illustrates a portion of the forceps 10. The forceps 10 can be connected to a source of electrosurgical energy (i.e., a generator; not shown) so that the forceps 10 function as electrosurgical forceps. The forceps 10 includes a gripping assembly 12 with a first jaw member 14 and art opposing second jaw member 16. As perhaps best understood by referring to both FIGS. 1 and 4, each jaw member 14, 16 includes a respective griping portion 18, 20 for gripping and coagulating a vessel or tissue 22 therebetween. Moreover, each jaw member 14, 16 includes an opening 48 at a distal end 46 thereof so that the blade 26 can extend or be extended there through. The blade 26 is located in a blade track 24 that runs between the jaw members 14, 16. While not specifically illustrated, it is understood that the forceps 10 also includes one or more mechanisms for actuating or moving one or both of the jaw members 14, 16 between an open position (FIG. 4) and a closed or clamped position (FIGS. 1 and 3), h is further understood that one or more mechanisms can be provided for actuating or moving the blade 26 between a retracted position (FIG. 1) and an extended position (FIG.).

Figure 2A:
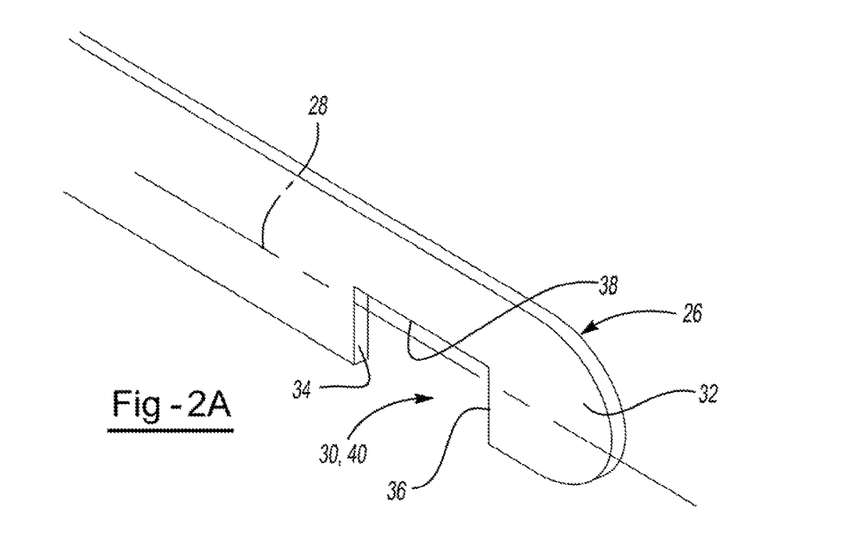
FIG. 2A is a partial perspective view of the blade according to the teachings herein.

FIG. 2A illustrates the blade 26. The blade 26 extends along a longitudinal axis 28 and includes a notched section 30 and a distal end 32. The notched section 30 includes a proximal edge 34, a distal edge 36, and an upper edge 38. One or more of the edges 34, 36, 38 define a receiving region 40. The edges 34, 36 extend generally perpendicular to the longitudinal axis 28.

Figure 2B:
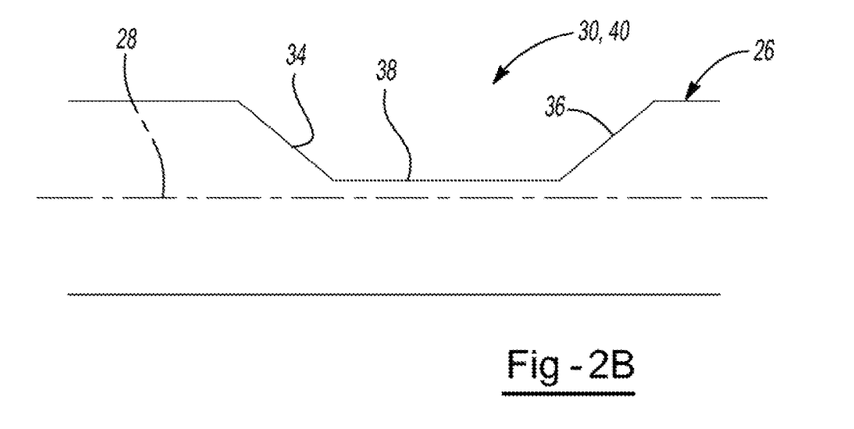
FIG. 2B is a partial perspective view of the blade according to the teachings herein.
Figure 2C:
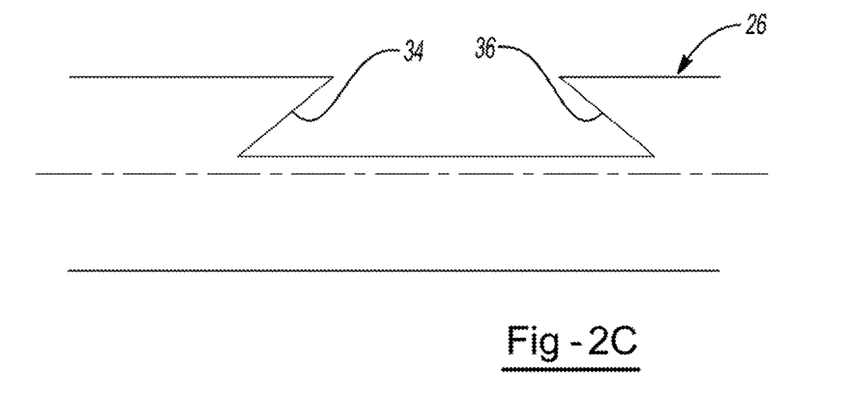
FIG. 2C is a partial perspective view of the blade according to the teachings herein.
Figure 2D:
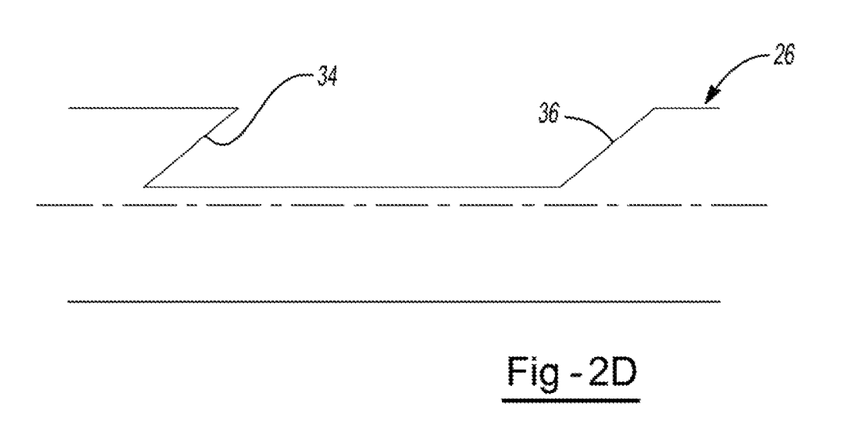
FIG. 2D is a partial perspective view of the blade according to the teachings herein.

FIGS. 2B, 2C, and 2D illustrate a portion of the blade 26 and the notched section 30 and receiving region 40. In FIG. 2B, the proximal edge 34 is distally canted relative to the axis 28 and the distal end of the blade 26, and the distal edge 36 is proximally canted relative to the axis 28 and the distal end of the blade 26. In FIG. 2C, the proximal edge 34 is proximally canted relative to the axis 28 and the distal end of the blade 26, and the distal edge 36 is distally canted relative to the axis 28 and the distal end of the blade 26. In FIG. 2D, the proximal edge 34 is proximally canted relative to the axis 28 and the distal end of the blade 26, and the distal edge 36 is proximally canted relative to the axis 28 and the distal end of the blade 26.

Figures 3, 4:
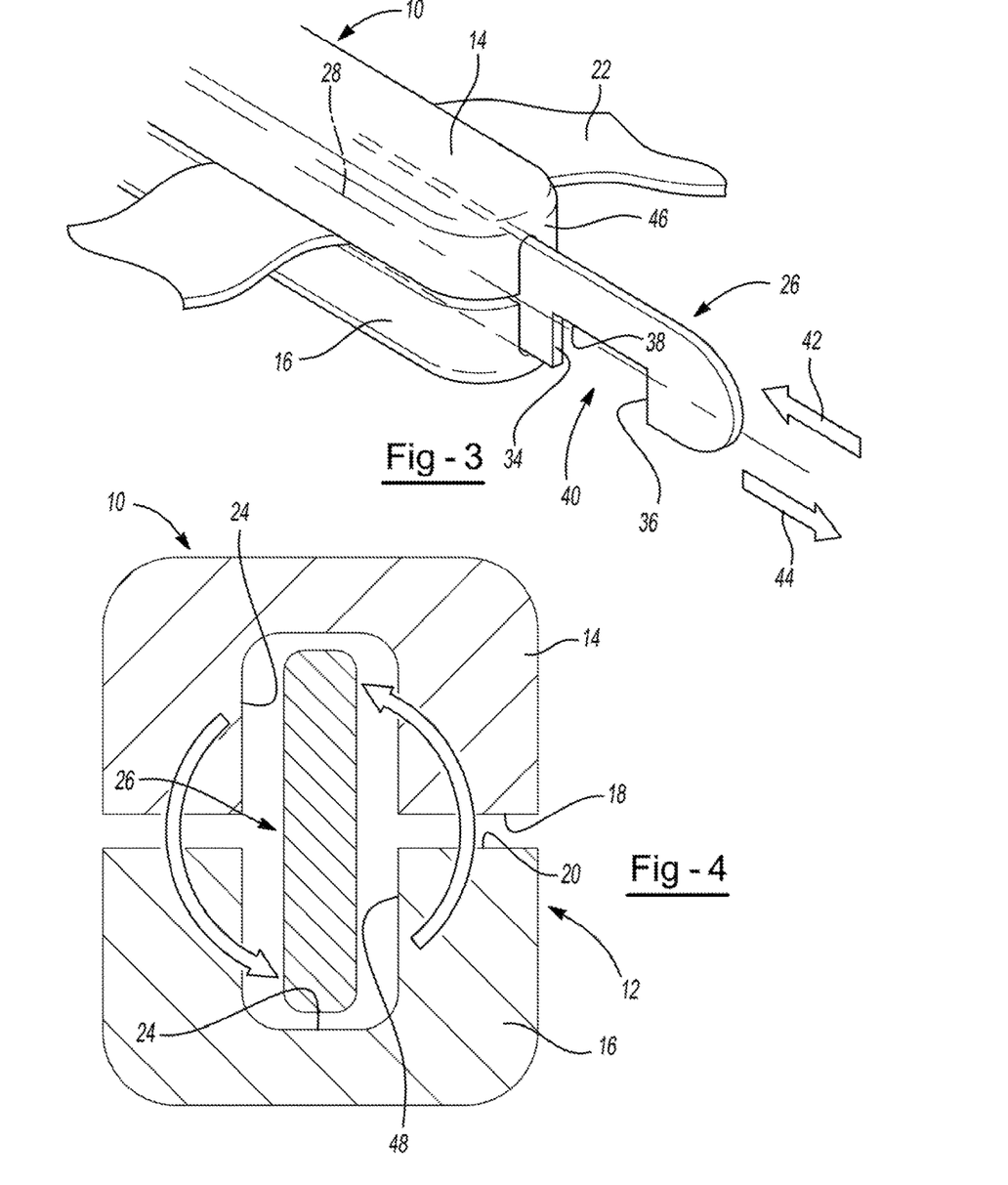
FIG. 3 is a partial perspective view of the forceps according to the teachings herein.
FIG. 4 is an end view of the forceps according to the teachings herein.
Figure 5A:
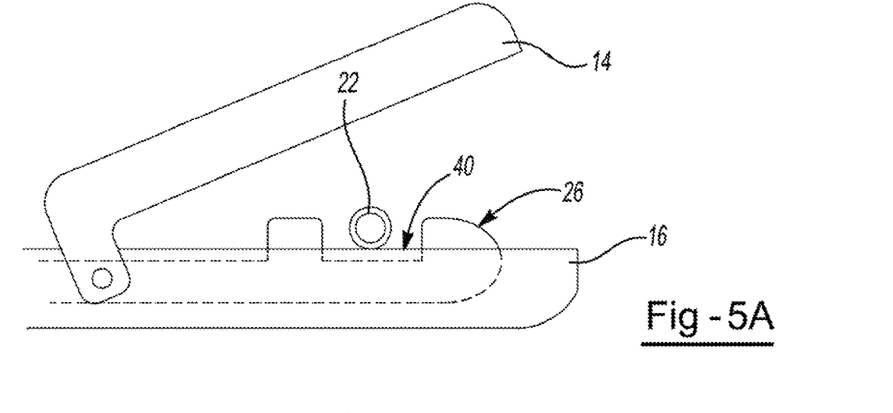
FIG. 5A is a side view of the forceps with the jaw members in an open position.
Figure 5B:
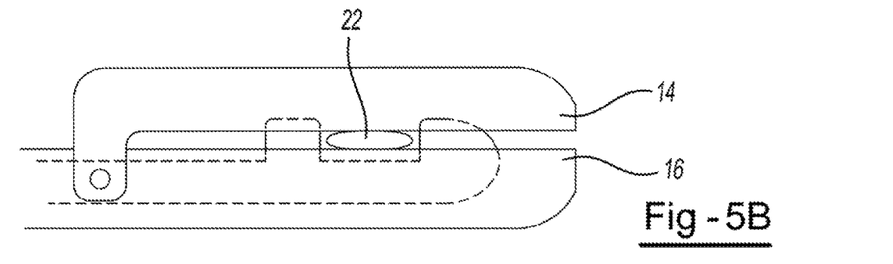
FIG. 5B is a side view of the forceps with the jaw members in the closed position.
Figure 5C:
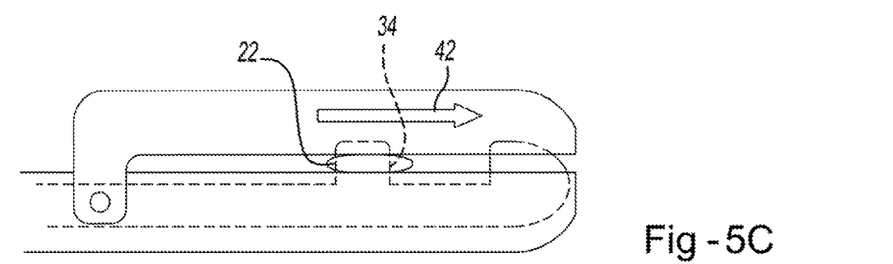
FIG. 5C is a side view of the forceps with the blade moved in the first direction.
Figure 5D:
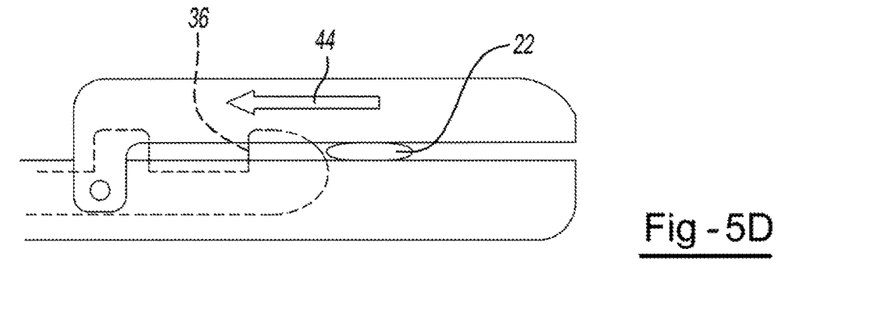
FIG. 5D is a side view of the forceps with the blade moved in the second direction.

FIG. 3 further illustrates portion of the forceps 10. The vessel or tissue 22 can be located between the jaw members 14, 16 and in the receiving region 40 of the blade 26 so that when the forceps 10 are in the closed or clamped position, the vessel or tissue 22 can be coagulated. Then, without having to reposition the forceps 10, while the forceps 10 are in the closed or clamped position, the blade 26 can be moved to cut or transect the vessel or tissue 22. That is, one or more of the edges 34, 36, 38 are sharp so that when the blade 26 is moved in a first direction 42, the vessel or tissue 22 can be transected with at least the proximal edge 34 of the notched section 30. When the blade 26 is moved in a second direction 44, the vessel or tissue 22 can be transected with at least the distal edge 36 of the notched section 30. The blade 26 can function as a blade electrode. FIG. 4 further illustrates a portion of the forceps 10. The blade 26 is rotatable (e.g., clockwise, counter-clockwise, or both) within the blade track 24 so that in a first rotated position, the notched section 30 (e.g., the upper edge 38) generally faces towards first jaw member 14. In a second rotated position, the notched section 30 (e.g., the upper edge 38) generally faces the second jaw member 16. The blade 26 is also rotatable to a position between the first and second rotated positions so that the notched section 30 (e.g., the upper edge 38) generally faces a position between the first jaw member 14 and the second jaw member 16.

With reference to the FIGS. 1-5D a method using the forceps 10 is illustrated. One or both of the jaw members 14, 16 may be connected to a source of electrosurgical energy (i.e., a generator; not shown). A doctor or surgeon can adjust the position of the blade 26 and the notched section 30 by rotating the blade 26 so that the upper edge 38 faces the first jaw member 14, the second jaw member 16, or faces a position between the jaws 14, 16. A tissue or vessel 22 may be grasped between the first and second jaw members 14, 16. The first jaw member 14 can be closed about the tissue or vessel 22 onto the second jaw member 16 (FIGS. 1 and 5B). It is understood that in other configurations, the second jaw member 16 can be closed onto the first jaw member 14, or both jaw members 14, 16 can be moved towards one another into a closed position. The forceps 10 may be activated to treat or coagulate the vessel or tissue 22 in a monopolar or bipolar configuration with a suitable therapy current from an energy source. However, it is understood that the vessel or tissue 22 need not be treated with a monopolar or bipolar energy. That is, the tissue or vessel 22 may be grasped between the first and second jaw members 14, 16 without activating or passing any energy or current to or through the tissue or vessel 22. With the jaws 14, 16 are in a closed position, the blade 26 can be moved so that the vessel or tissue 22 can be cut or transected with the notched section 30, without repositioning or moving the jaw members 14, 16. That is, the blade 26 can be moved distally in the first direction 42 (FIG. 5C) so that the vessel or tissue 22 is cut with at least the proximal edge 34 of the notched section 30, or the blade 26 can be moved proximally in the second direction 44 (FIG. 5D) so that the vessel or tissue 22 is cut or transected with at least the distal edge 36 of the notched section 30, in other configurations, one or both of the edges 34, 36 may be blunt or dull, and the cutting or transecting may occur with the therapy current that is provided to the blade 26. That is, when the blade 26 is moved in one of the directions 42, 44 and the corresponding edge 34, 36 contacts the tissue or vessel 22, the therapy current provided to the blade 26 may perform the cut.

In another configuration, the blade 26 or a separate blade member can extend beyond a distal end 46 of the forceps 10. Accordingly, the blade 26 or a separate blade member can be used as an electrode blade. When the blade 26 or a separate blade member is selected as an electrode blade, the first and second, aw members 14, 16 may be electrically deactivated.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

LISTING OF REFERENCE NUMERALS 10 forceps
12 gripping assembly
14 first jaw member
16 second jaw member
18 gripping portion (first jaw member 14)
20 gripping portion (second jaw member 16)
22 vessel or tissue
24 blade track
26 blade
28 longitudinal axis
30 notched section
32 distal end
34 proximal edge 36 distal edge
38 upper edge
40 receiving region
42 first direction
44 second direction
46 distal end of forceps 10
48 opening at distal end 46 of forceps 10

The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

The omission in the following claims of any aspect of subject matter that is disclosed herein is not a disclaimer of such subject matter, nor should it be regarded that the inventors did not consider such subject matter to be part of the disclosed inventive subject matter.

The invention claimed is:

1. A surgical device comprising:
   a. forceps including:
      i. a first working jaw, and
      ii. a second working jaw; and
   b. a blade extending along a longitudinal axis and located between the first working jaw and the second working jaw, the blade including:
      i. a notched section, the notched section comprising a proximal edge and a distal edge, at least one of the proximal edge and the distal edge is linear and generally perpendicular to the longitudinal axis, the notched section comprises an upper edge extending between the proximal edge and the distal edge,
   wherein the blade is moveable along the longitudinal axis while tissue is gripped between the first working jaw and the second working jaw so, that the tissue is cut with the proximal edge or the distal edge of the notched section without repositioning the first working jaw, the second working jaw, or both,
   wherein the blade is a blade electrode that is configured to deliver a first therapy current,
   wherein a distal end of the blade electrode is moveable beyond a distal-most end of the forceps so that that the distal end of the blade electrode functions as an electrosurgical blade,
   wherein the blade is rotatable between a first rotated position and a second rotated position, and
   wherein in the first rotated position, the upper edge of the notched section faces either the first working jaw or the second working jaw, and in the second rotated position the upper edge of the notched section faces a direction between the first working jaw and the second working jaw.

2. The surgical device of claim 1, wherein the first working jaw, the second working jaw or both is/are configured to deliver a second therapy current so that the tissue gripped between the first working jaw and the second working jaw and within the notched section can be coagulated with the second therapy current.

3. The surgical device of claim 1, wherein the first therapy current is a monopolar therapy current.

4. The surgical device of claim 1, wherein both of the proximal edge and the distal edge are linear and generally perpendicular to the longitudinal axis that the blade moves along.

5. The surgical device of claim 1, wherein the distal end of the blade electrode is dull.

6. The surgical device of claim 1, the blade is moveable in a distal direction along the longitudinal axis while the tissue is gripped between the first working jaw and the second working jaw so that the tissue is cut with the proximal edge without repositioning the first working jaw, the second working jaw, or both; and
   wherein the blade is moveable in a proximal direction along the longitudinal axis while the tissue is gripped between the first working jaw and the second working jaw so that the tissue is cut with the distal edge without repositioning the first working jaw, the second working jaw, or both.

7. The surgical device of claim 1, wherein the blade electrode is located inside a blade track that extends in the first working jaw, or the second working jaw, or both, so that the blade electrode is located in-between the first working jaw and the second working jaw.

8. An electrosurgical device comprising:
   a. forceps including:
      i. a first working jaw, and
      ii. a second working jaw; and
   b. a blade electrode located inside a blade track that extends in the first working jaw or the second working jaw, or both, so that the blade electrode is located in-between the first working jaw and the second working jaw, the blade electrode including:
      i. a notched section having a proximal edge, a distal edge and a receiving region therebetween, the notched section also having an upper edge extending between the proximal edge and the distal edge;
   wherein the first working jaw, the second working jaw, or both is/are configured to deliver a first therapy current so that during an application of the first therapy current, tissue located within the receiving region and gripped between the first working jaw and the second working jaw is coagulated,
   wherein the blade electrode is moveable so that the tissue located within the receiving region of the notched section is cut with either the proximal edge or the distal edge without repositioning the forceps,
   wherein the blade electrode is rotatable between a first rotated position and a second rotated position,
   wherein in the first rotated position, the upper edge of the notched section faces the first working jaw or the second working jaw, and in the second rotated position the upper edge of the notched section faces a direction between the first working jaw and the second working jaw, and
   wherein the blade electrode is configured to deliver a second therapy current so that during an application of the second therapy current, the blade electrode functions as an electrosurgical blade when at least a portion of the blade electrode extends beyond a distal-most end of the forceps.

9. The electrosurgical device of claim 8, wherein the blade electrode extends along a longitudinal axis, and the proximal edge, the distal edge, or both extend generally perpendicular to the longitudinal axis, and wherein the blade electrode is moveable along the longitudinal axis to cut the tissue located within the receiving region of the notched section.

10. The electrosurgical device of claim 8, wherein the blade electrode is moveable towards a proximal end of the forceps so that the tissue located within the receiving region of the notched section is cut with the distal edge of the notched section, and wherein the blade electrode is moveable towards the distal end of the forceps so that the tissue located within the receiving region of the notched section is cut with the proximal edge of the notched section.

11. The electrosurgical device of claim 8, wherein the distal edge faces the proximal edge, and the distal edge is spaced apart in a distal direction from the proximal edge along the longitudinal axis.

12. A device comprising:
   a. forceps including:
      i. a first working jaw, and
      ii. a second working jaw; and
   b. a blade extending along a longitudinal axis and located between the first working jaw and the second working jaw, the blade including:
      iii. a notched section, the notched section comprising a proximal edge and a distal edge, wherein the distal edge faces the proximal edge, wherein the distal edge is spaced apart from the proximal edge in a distal direction along the longitudinal axis, wherein the first working jaw, the second working jaw, or both is/are configured to deliver a bipolar therapy current so that tissue gripped between the first working jaw and the second working jaw and within the notched section can be coagulated with the bipolar therapy current, wherein the blade is moveable in a proximal direction along the longitudinal axis while the tissue is gripped between the first working jaw and the second working jaw so that the tissue is cut with the distal edge without repositioning the first working jaw, the second working jaw, or both, wherein the blade is moveable in a distal direction along the longitudinal axis while the tissue is gripped between the first working jaw and the second working jaw so that the tissue is cut with the proximal edge without repositioning the first working jaw, the second working jaw, or both, wherein the blade is a blade electrode is configured to deliver a monopolar therapy current, wherein a distal end of the blade electrode is moveable beyond a distal end of the forceps so that that the distal end of the blade electrode functions as an electrosurgical blade, wherein the blade is rotatable between a first rotated position and a second rotated position, wherein in the first rotated position, the notched section faces either the first working jaw or the second working jaw, and in the second rotated position the notched section faces a direction between the first working jaw and the second working jaw.

13. The device of claim 12, wherein one or both of the proximal edge and the distal edge are canted relative to the longitudinal axis.

14. The device of claim 12, wherein one or both of the proximal edge and the distal edge are perpendicular to the longitudinal axis.

15. The device of claim 12, wherein the proximal edge and the distal edge are generally parallel to each other.

16. The device of claim 12, wherein the proximal edge and the distal edge are canted relative to the longitudinal axis.

17. The device of claim 12, wherein the blade electrode is located inside a blade track that extends in the first working jaw, or the second working jaw, or both, so that the blade electrode is located in-between the first working jaw and the second working jaw.

18. The device of claim 12, wherein the distal end of the blade electrode is dull.

* * * * *